United States Patent [19]

Ilsink

[11] Patent Number: Plant 7,430

[45] Date of Patent: Jan. 29, 1991

[54] MINIATURE ROSE PLANT NAMED INTERGOL

[75] Inventor: G. P. Ilsink, Leersum, Netherlands

[73] Assignee: Interflant B.V., Leersum, Netherlands

[21] Appl. No.: 392,577

[22] Filed: Aug. 11, 1989

[51] Int. Cl.[5] ..... A01H 5/00

[52] U.S. Cl. ..... Plt./8

[58] Field of Search ..... Plt. 8

*Primary Examiner*—James R. Feyrer

*Attorney, Agent, or Firm*—Christie, Parker & Hale

[57] ABSTRACT

A new variety of miniature rose having deep yellow flowers produced on a good pot forcing plant also suitable for growing outdoors in gardens.

2 Drawing Sheets

SUMMARY OF THE INVENTION

The present invention relates to a new and distinct variety of rose plant of the miniature rose class, which was originated by me by crossing as seed parent an unnamed, unpatented seedling of my creation, and as pollen parent the rose known as "Colibri". The varietal denomination of the new variety is "Intergol".

Among the novel characteristics possessed by this new variety which distinguish it from its parent and all other varieties of which I am aware are its deep yellow flowers borne on a plant particularly suited for production of flowering pot plants and for growing in outdoor gardens. "Intergol" can also be reproduced through propagation by cuttings, grafting and budding. Flowers of the new variety are long lasting on the plant. Asexual reproduction by budding, grafting and propagation of cuttings of the new variety as performed in Hazerswoude, Holland, shows that the foregoing and other distinguishing characteristics come true to form and are established and transmitted through succeeding propagation.

The accompanying illustrations show typical specimens of the vegetative growth and flowers of the new variety in different stages of development and depicted in color as nearly true as it is reasonably possible to make the same in a color illustration of this character. However, the color shown in FIG. 1 is a truer representation.

BRIEF DESCRIPTION OF THE DRAWINGS

FIG. 1 is an illustration of a plant of the new variety of miniature rose showing flowering and growth habit and with more typical flower coloring;

FIG. 2 is an illustration showing details of the new miniature rose variety, but with flower coloring deeper than true.

DESCRIPTION OF PREFERRED EMBODIMENT

The following is a detailed description of my new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart.

Parentage: Seedling.

*Seed parent.*—Unnamed seedling.

*Pollen parent.*—"Colibri".

Class: Miniature.

As can be seen in the accompanying illustrations, FIG. 1 shows one sample of flowering plant of "Intergol" depicting the pot plant habit of growth and flowering. Since flowering is nearly continuous, the floriferous "Intergol" can remain attractively in bloom for long periods when given proper care and culture.

The illustration in FIG. 2 shows details of the new variety "Intergol". In the illustration there is shown the top of a young shoot, 1; compound three, five and seven leaflet leaves, 2, 3, and 4, respectively; a stem 5; a green bud, 6; a flower bud, 7, after sepals separate; a flower 8 about one-third to one-half open; and a flower, 9, fully open. Also shown are flower stems 10, 11, and 12, with reproductive organs.

The following further horicultural observations were made of specimens grown outdoor in Holland.

FLOWER

Blooming habit: Nearly continuous.

A. Bud:

(1) *Size.*—Medium.

(2) *Form.*—Pointed, ovate (before separation of sepals).

(3) *Color.*—As sepals divide, bud color is near 12A.

(4) *Sepals.*—Longer than bud, simple to slightly foliated.

(5) *Penduncle.*—Length — about 3 to 4.5 cm. Aspect — straight. Strength — erect. Color — medium green.

B. Bloom:

*Flower.*—Average size for miniature; viewed from above — round; viewed from side: (A) upper part of fully opened flower — flat to flattened convex; (B) lower part of fully opened flower — flattened convex.

(1) *Size.*—Average size when fully expanded — about 5 cm.

(2) *Borne.*—Singly, one to a stem.

(3) *Form.*—Ovoid to cupped at first, becoming flat; outer petals reflex and quill to points; inner petals reflex and roll under slightly.

(4) *Petalage.*—Number of petals under normal conditions — about 20 to 24, semi-double.

(5) *Color.*—After sepals separate, near 12A to B; when sepals part and petals begin to unfurl, predominant color is near 12A to B, deeper toned where petals bunch; viewing petals' top surface in $\frac{1}{3}$ to $\frac{1}{2}$ open stage, color surface is near 12A to B to 13B. Color through this range is substantially stable. Petal's top and reverse sides are of similar coloring but under surface may be somewhat deeper toned, near 13B to C. Outer petals occasionally show markings of red shades, near 47D. Coloring at point of petal attachment is near 13A to B. Overall tonality from a distance is an attractive deep yellow.

(6) *Pedicel.*—Medium number of hairs or prickles.

C. Petals:

(1) *Texture.*—Medium.

(2) *Appearance.*—Inside velvety and outside satiny.

(3) *Form and size.*—Broad obovate.

(4) *Arrangement.*—Regularly arranged, imbricated.

(5) *Petaloids in center.*—Several.

(6) *Persistence.*—Drop off cleanly.

(7) *Fragrance.*—Slight to none.

(8) *Lasting quality.*—Long lasting quality on plant.

REPRODUCTIVE ORGANS

A. Stamens, filaments and anthers:

*Arrangement and color.*—Regularly arranged around styles; color — filaments orange.

B. Pollen:

*Color.*—Yellow orange.

C. Styles: Even, medium length, red, upper half little to no hairs, bunched.

D. Stigma: Full, positioned below anthers.

E. Hips: Small, pitcher-shaped.

PLANT

A. Form: Bushy.

B. Growth: Vigorous; height attained, about 20 to 24 cm.

C. Foliage: Compound 3, 5 and 7 leaflets.

(1) *Size.*—Medium for a miniature.

(2) *Quantity.*—Abundant.

(3) *Color.*—Foliage at time of first flowering — medium green.

(4) *Shape.*—Oval, pointed.

(5) *Texture.*—Upper side is medium glossy; under side is matte.

(6) *Edge.*—Serrate.

(7) *Serration.*—Ordinary, acuminate apices.

(8) *Leaf stem.*—Color — medium green.

(9) *Stipules.*—Short, simple, medium to light green, distinct auricle.

(10) *Leaflet.*—Cross section — flat, medium undulation at margin; terminal leaflet — short to very short, narrow, rounded base; petiole — short.

D. Wood:

(1) *New wood.*—Color — medium green.

(2) *Old wood.*—Color — medium green.

E. Prickles (thorns):

(1) *Prickles.*—Present, quantity (main stalk) — ordinary; on laterals from stalk — few; form — straight and slanted slightly downward, slight recurved; shape of upper side — flat; shape of lower side — deep concave; length — many $\leqq 5$ mm; few $> 5$ mm; color — tan to pale pink; position — irregular.

F. Winter hardiness: Needs protection outdoors in severe climates.

I claim:

1. A new and distinct variety of rose plant of the miniature rose class, substantially as shown and described, characterized particularly by a plant suitable for growing in pots and outdoor in gardens and by attractive deep yellow flowers which are long lasting on the plant.

* * * * *

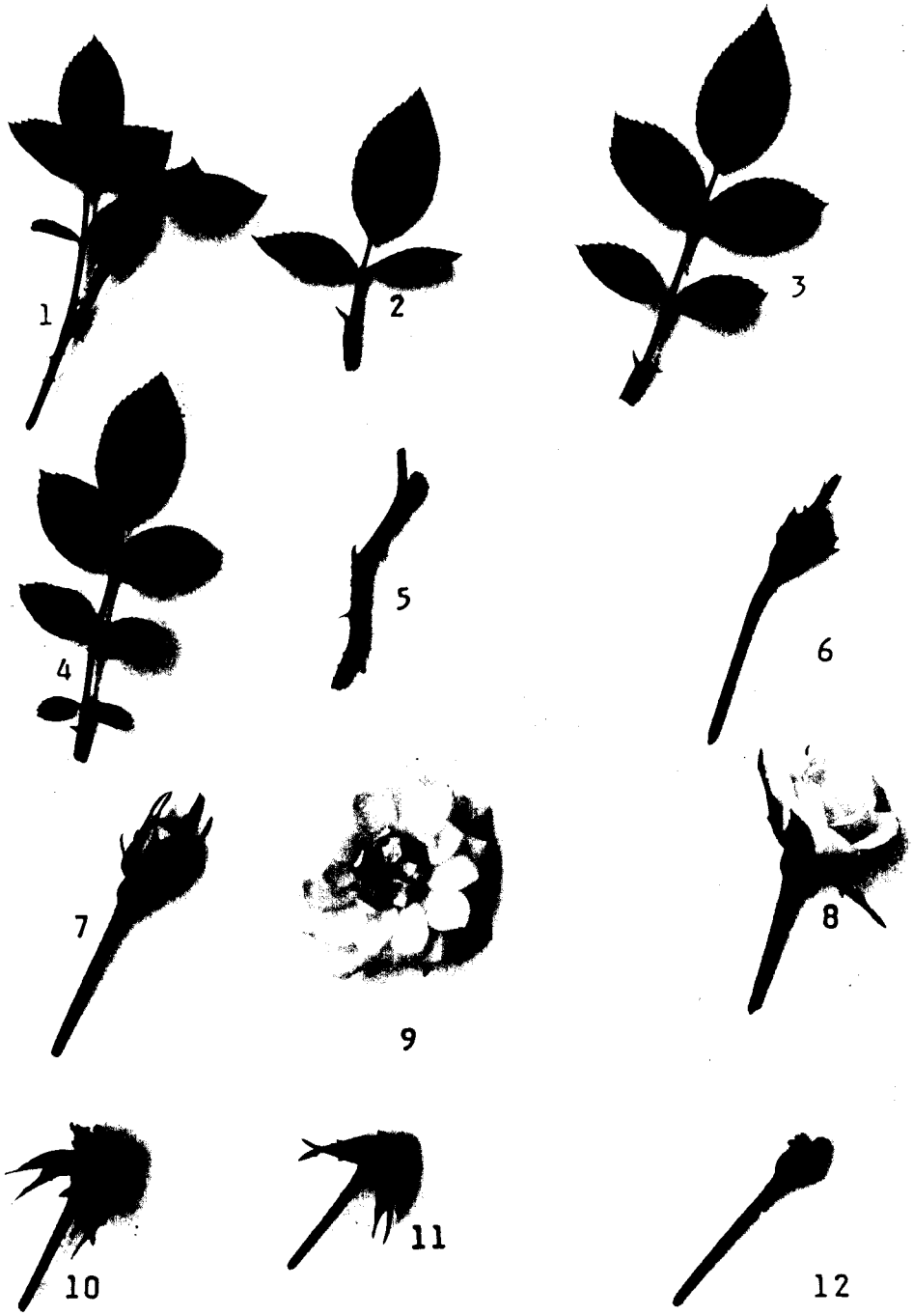
INTERGOL
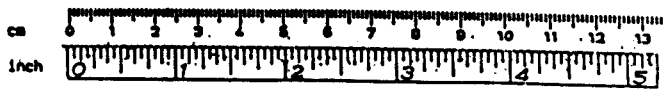

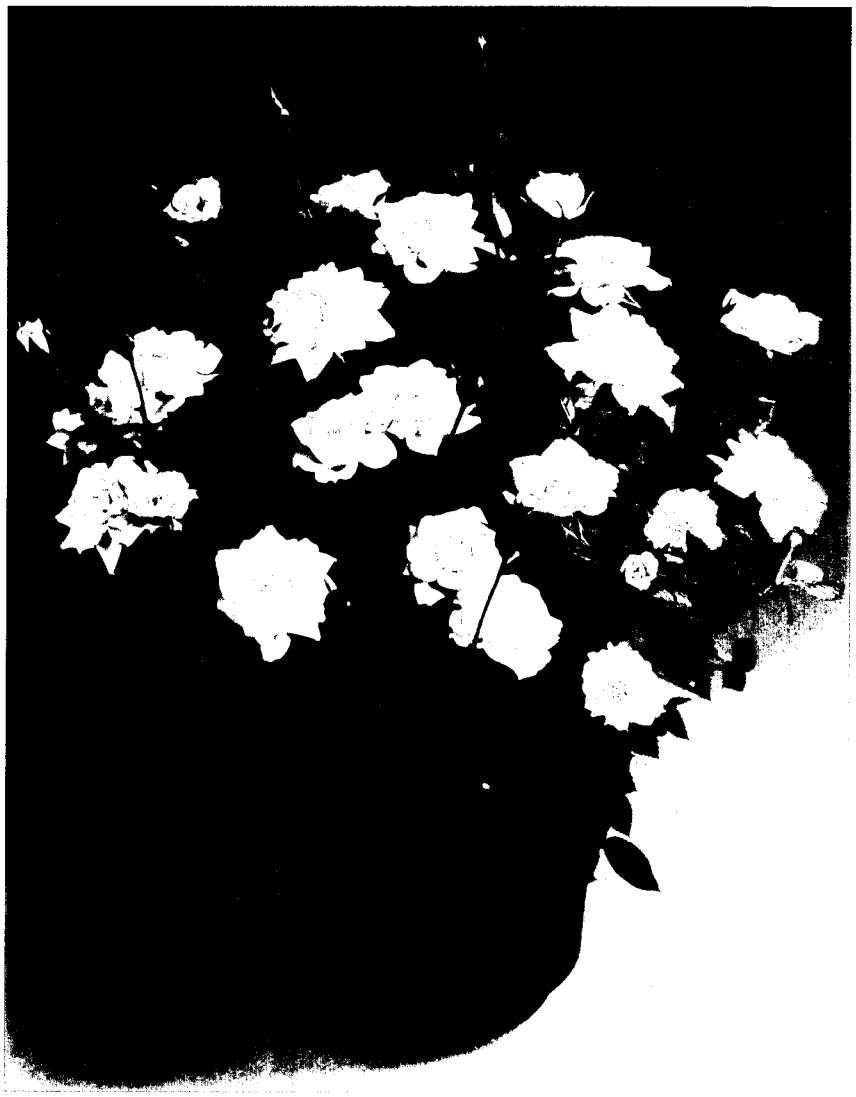

UNITED STATES PATENT AND TRADEMARK OFFICE

CERTIFICATE OF CORRECTION

PATENT NO. : Plant 7,430

DATED : January 29, 1991

INVENTOR(S) : G.P. Ilsink

It is certified that error appears in the above-identified patent and that said Letters Patent is hereby corrected as shown below:

Column 2, line 24, before "FLOWER" insert -- 1. --

Column 3, line 27, before "REPRODUCTIVE ORGANS" insert -- 2 --.

Column 3, line 41, before "PLANT" insert -- 3. --.

Column 4, line 1, after "attained" change the period to a comma.

Signed and Sealed this

Twentieth Day of October, 1992

*Attest:*

*Attesting Officer*

DOUGLAS B. COMER

*Acting Commissioner of Patents and Trademarks*